United States Patent [19]
Doi et al.

[11] Patent Number: 5,908,865
[45] Date of Patent: Jun. 1, 1999

[54] CHLORHEXIDINE GLUCONATE-CONTAINING, STABILIZED AQUEOUS PHARMACEUTICAL PREPARATIONS

[75] Inventors: Koji Doi; Hiroshi Aki, both of Kobe, Japan

[73] Assignee: Senju Pharmaceutical Co., Ltd., Japan

[21] Appl. No.: 08/855,586

[22] Filed: May 13, 1997

[30] Foreign Application Priority Data

May 13, 1996 [JP] Japan .................................. 8-143616

[51] Int. Cl.$^6$ .................................................. A01N 37/52
[52] U.S. Cl. ............................................................ 514/635
[58] Field of Search .............................. 424/433; 514/635

[56] References Cited

U.S. PATENT DOCUMENTS

| 5,466,463 | 11/1995 | Ford | ........................................ 435/853 |
| 5,626,837 | 5/1997 | Shimada et al. | ........................... 424/49 |

*Primary Examiner*—Jose' G. Dees
*Assistant Examiner*—Alton Pryor
*Attorney, Agent, or Firm*—Millen, White, Zelano & Branigan, P.C.

[57] ABSTRACT

An aqueous pharmaceutical preparation is provided containing chloride ion and stably containing chlorhexidine gluconate, characterized in that said preparation further contains at least one pharmaceutically acceptable polycarboxylic acid of the formula I:

$$HOOC-(CR_{i1}-CR_{i2})_n-COOH \qquad (I)$$

wherein n is an integer 1, 2 or 3; i is a positive integer not more than n; $R^{11}$ and $R_{12}$, when n=1, independently from each other, are H, —OH or —COOH; each of $R_{11}$, $R_{12}$, $R_{21}$ and $R_{22}$, when n=2, is H, —OH or —COOH, but not all of them are H simultaneously; and each of $R_{11}$, $R_{12}$, $R_{21}$, $R_{22}$, $R_{31}$ and $R_{32}$, when n=3, is H, —OH or —COOH, but two adjacent carbons in no case contain four hydrogen atoms in total; or a pharmaceutically acceptable salt thereof.

24 Claims, No Drawings

CHLORHEXIDINE GLUCONATE-CONTAINING, STABILIZED AQUEOUS PHARMACEUTICAL PREPARATIONS

FIELD OF THE INVENTION

The present invention relates to stabilization of chlorhexidine gluconate-containing aqueous pharmaceutical preparations.

BACKGROUND OF THE INVENTION

Due to its antimicrobial activity, chlorhexidine gluconate, a salt of chlorhexidine with gluconic acid, is widely used in forms of aqueous solutions as local disinfectants for disinfection of fingers and skin, and disinfection of the site of surgery, disinfection of surgical tools, as well as for disinfection of operation rooms and sickrooms, washing and disinfection of conjunctival sac, disinfection of the skin on and around external genitalia. In addition, chlorhexidine gluconate is also widely used as a preservative to prevent growth of microorganisms in aqueous pharmaceutical preparations for external use and preparations for topical use such as, eye drops and nasal drops.

However, chlorhexidine gluconate by nature is prone to develop precipitates by forming scarcely soluble salts where other anions than gluconate are present. For instance, it is known that chlorhexidine gluconate aqueous solutions will develop precipitates over time in the presence of citrate or chloride ion. Therefore, either of citrate or chloride ion is an incompatible chemical species with chlorhexidine.

On the other hand, in most of the cases, aqueous pharmaceutical preparations such as eye drops and nasal drops contain chloride ion. A number of active drugs and excipients provide a source of chloride ion, such as, sodium chloride as an isotonic agent; inorganic chlorides such as potassium chloride, calcium chloride, and magnesium chloride; compounds used as pharmacologically active constituents such as pilocarpine hydrochloride (miotic), pyridoxine hydrochloride (vitamin $B_6$), naphazoline hydrochloride (vasoconstricter), diphenhydramine hydrochloride (antihistamine), dibucaine hydrochloride (local anesthetic); and hydrochloric acid used as a pH adjusting agent during production of aqueous pharmaceutical preparations. Thus, inclusion of chloride ion is unavoidable in many of aqueous pharmaceutical preparations.

Therefore, in many of aqueous pharmaceutical preparations such as eye drops and nasal drops, it has been unallowable to simply employ chlorhexidine gluconate as a preservative.

In order to prevent precipitation of chlorhexidine in a chloride ion-containing aqueous solution, it is known to include a nonionic surface active agent in the solution. However, as nonionic surface active agents are prone to cause irritation to mucous membrane, it is unfavorable to include a nonionic surface active agent in preparations to be applied to mucous membranes such as, in particular, eye drops or nasal drops.

Thus, there exists a need for a method of maintaining, without inclusion of nonionic surface active agent, chlorhexidine gluconate stably in an aqueous pharmaceutical preparation in concurrent presence of chloride ion, as well as for an aqueous pharmaceutical preparation produced by such a method.

SUMMARY OF THE INVENTION

It is the objective of the present invention to provide a method for producing aqueous pharmaceutical preparations stably containing chlorhexidine gluconate in solution despite inclusion of chloride ion, and to thereby provide such aqueous pharmaceutical preparations.

The present inventors unexpectedly discovered that chlorhexidine gluconate can be stably, i.e. without formation of precipitation over time, maintained in an aqueous solution even in the presence of chloride ion, which is generally incompatible with chlorhexidine gluconate aqueous solution, by means of concurrent inclusion of a type of polycarboxylic acid of the following formula I or its salt, which includes citric acid and citrate, compounds also incompatible with chlorhexidine gluconate.

$$\text{HOOC—(CR}_{i1}\text{R}_{i2}\text{)n—COOH} \qquad (I)$$

In formula I, n is an integer 1, 2 or 3; i is a positive integer not more than n; $R_{11}$ and $R_{12}$, when n=1, independently from each other, are H, —OH or —COOH; each of $R_{11}$, $R_{12}$, $R_{21}$ and $R_{22}$, when n=2, is H, —OH or —COOH, but not all of them are H simultaneously; and each of $R_{11}$, $R_{12}$, $R_{21}$, $R_{22}$, $R_{31}$ and $R_{32}$, when n=3, is H, —OH or —COOH, but two adjacent carbons in no case contain four hydrogen atoms in total.

Thus, the present invention provides an aqueous pharmaceutical preparation containing chloride ion and chlorhexidine gluconate wherein chlorhexidine gluconate is stably contained, characterized in that said preparation further contains at least one pharmaceutically acceptable polycarboxylic acid of the formula I:

$$\text{HOOC—(CR}_{i1}\text{R}_{i2}\text{)n—COOH} \qquad (I)$$

wherein n denotes an integer of 1 to 3; i denotes a positive integer not more than n; $R_{11}$ and $R_{12}$, when n=1, independently from each other, denote H, —OH or —COOH; each of $R_{11}$, $R_{12}$, $R_{21}$ and $R_{22}$ when n=2, denotes H, —OH or —COOH with the proviso that not all of them denote H simultaneously; and each of $R_{11}$, $R_{12}$, $R_{21}$, $R_{22}$, $R_{31}$ and $R_{32}$, when n=3, denotes H, —OH or —COOH with the proviso that two adjacent carbons in no case contain four hydrogen atoms in total; or a pharmaceutically acceptable salt thereof.

Further, the present invention also provides a method for prevention of precipitation of chlorhexidine gluconate in an aqueous solution containing chloride ion and chlorhexidine gluconate, characterized by further inclusion in said aqueous solution of at least one polycarboxylic acid of the formula I:

$$\text{HOOC—(CR}_{i1}\text{R}_{i2}\text{)n—COOH} \qquad (I)$$

wherein n, i, $R_{i1}$ and $R_{i2}$ are as defined hereinbefore; or a pharmaceutically acceptable salt thereof.

DETAILED DESCRIPTION OF THE INVENTION

Particularly preferred examples of the polycarboxylic acid as defined above include oxalic acid, citric acid, malic acid and tartaric acid. For polycarboxylic acids including optically active isomers, such as malic acid and tartaric acid, either of D- or L-enantiomer as well as racemic mixture may be used. However, where it is intended to apply the aqueous pharmaceutical preparation to a local mucous membrane or a wound site, optical isomers of naturally occurring types are more preferred. Examples of preferred pharmaceutically acceptable salts of polycarboxylic acid include, but no limited to, sodium, potassium, calcium and ammonium salts.

Polycarboxylic acids as above-defined are used at a concentration of preferably 0.01–5 W/V %, more preferably 0.05–3 W/V %, still more preferably 0.1–1 W/V %, and most preferably 0.2–0.5 W/V %.

The concentration range of chlorhexidine gluconate within which it can be stably contained according to the present invention is fairly wide, so that chlorhexidine gluconate can be stably included at 0.05 W/V %, which is a usual concentration used for disinfection of wound site of the skin, or lower. Thus, 0.05 W/V % and lower is the preferable concentration range for chlorhexidine gluconate in the practice of the present invention. In stabilizing chlorhexidine gluconate, its lower limit is not an issue, thus even a concentration as low as 0.0001 W/V % is allowable. Further, a concentration range of 0.0005–0.025 W/V %, which covers the concentration used for disinfection of external genitalia, is also preferable.

The concentration of chloride ion present in the aqueous pharmaceutical preparation of the present invention may be 0.05–200 mEq/L.

The present invention eliminates the need of inclusion of nonionic surface active agents, which have been required for prevention of precipitation where chloride ion is contained in an aqueous pharmaceutical preparation containing chlorhexidine gluconate, as an active principle or as a preservative, and it makes it possible to reduce the amount of a nonionic surface active agent even when one is included. As nonionic surface active agents lowers the antimicrobial activity of chlorhexidine gluconate, the present invention, which eliminates the need of inclusion of nonionic surface active agents, allows to provide chlorhexidine gluconate containing aqueous pharmaceutical preparations superior to those available heretofore. The present invention will be described in further detail below.

Stability Tests

[Stability Test 1] Chloride ion-induced precipitation of chlorhexidine over time In order to evaluate, with the aid of an acceleration test, whether precipitation of chlorhexidine gluconate will occur over time in the presence of chloride ion in a solution, a repetitive freezing-thawing test was performed on solutions containing chlorhexidine gluconate. Aqueous solutions containing 0.005 W/V % of chlorhexidine gluconate and 0.5 W/V % of one of chloride ion-releasing compounds, "a"–"g" described below, with pH of approximately 6, were prepared as test solutions (test solutions "a"–"g") and used in 15-ml PET (polyethylene terephthalate) containers. Separately, a solution identical to these solutions except that it did not contain a chloride ion-releasing compound was prepared and used likewise as a control solution. For both the test and control solutions, freezing and thawing were repeated up to five cycles between −20° C. and room temperature, and the solutions were examined for precipitation in accordance with The Test for Insoluble Foreign Matters, in The Japanese Pharmacopoeia, 12th edition, General Rules for Pharmaceuticals, Eye Drops (8) (Hirokawa Publishing Co., 1991).

The chloride ion releasing compounds used and their chloride ion concentrations (mEq/L) for the test solutions "a"–"g" were as follows.

a) Sodium chloride (85.5 mEq/L)
b) Potassium chloride (90.1 mEq/L)
c) Magnesium chloride (105.0 mEq/L)
d) Naphazoline hydrochloride (20.3 mEq/L)
e) Dibucaine hydrochloride (13.2 mEq/L)
f) Pyridoxine hydrochloride (24.3 mEq/L)
g) Benzalkonium chloride (12.9–20.2 mEq/L)

Results: While no precipitation was noted in the control solution after the five-cycle freezing-thawing test, any of the test solutions a–g containing chloride ions at different concentrations developed precipitates after a single cycle. The results support that chloride ion is incompatible with the chlorhexidine gluconate.

[Stability Test 2] The effect of sodium citrate against chloride ion-induced chlorhexidine gluconate precipitation over time.

In order to examine an effect of sodium citrate against chloride ion-induced precipitation over time, a repetitive freezing-thawing test was performed. Aqueous solutions containing 0.005 W/V % of chlorhexidine gluconate, 0.5 W/V % of sodium chloride, and 0.01, 0.05, 0.1, 0.2, 0.5, 1, 5 or 10 W/V % of sodium citrate, with pH of approximately 6, were prepared as test solutions, and used in 15-ml PET containers. Separately, as a control solution, a solution was prepared likewise except for omission of sodium citrate, and used in the test in the same manner.

Results: While the control solution developed precipitates after a single cycle of freezing-thawing test between −20° C. and room temperature, development of precipitates was found suppressed in the test solutions. The results indicate that the citric acid and its salt are effective in prevention of chloride ion-induced, over-time precipitate formation of chlorhexidine gluconate.

[Stability Test 3] Effect of other polycarboxylic acid against chloride ion-induced chlorhexidine gluconate precipitation over time.

In order to examine the effects of other polycarboxylic acids than citric acid against chloride ion-induced precipitation over time, a repetitive freezing-thawing test was performed. Aqueous solutions containing 0.005 W/V % of chlorhexidine gluconate, 0.5 W/V % of sodium chloride, and, as a polycarboxylic acid, 0.2 W/V % of oxalic acid, L-tartaric acid or L-malic acid, with pH of approximately 6, were prepared as test solutions, and used in 15-ml PET containers. Separately, as a control solution, a solution was prepared likewise except for omission of polycarboxylic acid, and used in the test in the same manner.

Results: While the control solution produced precipitation after a single cycle of freezing-thawing test between −20° C. and room temperature, precipitation formation was not noted in the test solutions even after 10 cycles of the freezing-thawing test. The results indicate that oxalic acid, tartaric acid and malic acid are also comparably effective with, or more effective than, citric acid in the prevention of chloride ion-induced precipitation formation of chlorhexidine gluconate over time.

[Stability Test 4]

For comparison, succinic acid, which has two consecutive methylene repeating units between carboxyl groups, and fumaric acid, which has an ethylenic double bond, were respectively employed as a candidate polycarboxylic acid in the same manner as Stability Test 3 above, all the control and test solutions developed precipitates after a single cycle of freezing-thawing test.

As shown in Stability Tests 1–3 and 4, citric acid, oxalic acid, tartaric acid and malic acid were found effective in prevention of precipitation formation of chlorhexidine gluconate over time in a solution containing chloride ion, whereas no effect was observed in succinic acid or fumaric acid.

In addition, it was found that none of the above polycarboxylic acids having precipitation preventive effect impaired the antimicrobial activity of chlorhexidine gluconate.

EXAMPLES

The following are examples of aqueous pharmaceutical preparations according to the present invention, for which it has been confirmed that chlorhexidine gluconate is stably contained. Within the brackets are shown concentrations of chloride ion resulting from corresponding ingredients in mEq/L. In preparing each of the aqueous pharmaceutical preparations, chlorhexidine gluconate in the form of 20% aqueous solution was used.

[Example 1] Eye Drops

By a conventional method, the following components were mixed to form a solution, and then sterilized by filtration to give eye drops.

| | | |
|---|---|---|
| Naphazoline hydrochloride | 0.002 | g (0.008) |
| Allantoin | 0.1 | g |
| Chlorpheniramine maleate | 0.03 | g |
| Boric acid | 1.8 | g |
| Sodium citrate | 0.2 | g |
| Chlorhexidine gluconate | 0.005 | g |
| Borax or hydrochloric acid | q.s. | (to pH 6.1) |
| Purified sterile water | q.s. | |
| Total | 100 | mL |

[Example 2] Eye Drops

By a conventional method, the following components were mixed to form a solution, and then sterilized by filtration to give eye drops.

| | | |
|---|---|---|
| Neostigmine methyl sulfate | 0.005 | g |
| Pyridoxine hydrochloride | 0.1 | g (4.86) |
| Taurine | 1.0 | g |
| Chlorpheniramine maleate | 0.03 | g |
| Boric acid | 1.1 | g |
| Sodium citrate | 0.2 | g |
| Chlorhexidine gluconate | 0.0025 | g |
| Sodium hydroxide or hydrochloric acid | q.s. | (to pH 5.5) |
| Purified sterile water | q.s. | |
| Total | 100 | mL |

[Example 3] Eye Drops

By a conventional method, the following components were mixed to form a solution, and then sterilized by filtration to give eye drops.

| | | |
|---|---|---|
| Diphenhydramine hydrochloride | 0.05 | g (1.71) |
| Cyanocobalamin | 0.02 | g |
| Potassium L-aspartate | 1.0 | g |
| Conc. glycerol | 1.4 | g |
| Sodium citrate | 0.2 | g |
| Chlorhexidine gluconate | 0.005 | g |
| Sodium hydroxide or hydrochloric acid | q.s. | (to pH 6.0) |
| Purified sterile water | q.s. | |
| Total | 100 | mL |

[Example 4] Eye Drops

By a conventional method, the following components were mixed to form a solution, and then sterilized by filtration to give eye drops.

| | | |
|---|---|---|
| Neostigmine methyl sulfate | 0.005 | g |
| Flavin adenine dinucleotide | 0.05 | g |
| Cyanocobalamin | 0.02 | g |
| Sodium chloride | 0.9 | g (154) |
| Sodium citrate | 0.2 | g |
| Chlorhexidine gluconate | 0.0025 | g |
| Sodium hydroxide or hydrochloric acid | q.s. | (to pH 6.0) |
| Purified sterile water | q.s. | |
| Total | 100 | mL |

[Example 5] Eye Drops

By a conventional method, the following components were mixed to form a solution, and then sterilized by filtration to give eye drops.

| | | |
|---|---|---|
| Naphazoline hydrochloride | 0.003 | g (0.1) |
| Diphenhydramine hydrochloride | 0.1 | g (3.4) |
| Pyridoxine hydrochloride | 0.1 | g (4.9) |
| Sodium chloride | 0.8 | g (136.9) |
| Sodium citrate | 0.2 | g |
| Chlorhexidine gluconate | 0.0025 | g |
| Sodium hydroxide or hydrochloric acid | q.s. | (to pH 6.1) |
| Purified sterile water | q.s. | |
| Total | 100 | mL |

[Example 6] Nasal Drops

By a conventional method, the following components were mixed to form a solution, and then sterilized by filtration to give nasal drops.

| | | |
|---|---|---|
| Naphazoline hydrochloride | 0.05 | g (2.03) |
| Chlorpheniramine maleate | 0.5 | g |
| Sodium citrate | 0.2 | g |
| Chlorhexidine gluconate | 0.005 | g |
| Conc. glycerol | 2.1 | g |
| Sodium hydroxide or hydrochloric acid | q.s. | (to pH 6.0) |
| Purified sterile water | q.s. | |
| Total | 100 | mL |

[Example 7] Pharmaceutical Preparation for External Use

By a conventional method, the following components were mixed to form a solution to give a pharmaceutical preparation for external use.

| | | |
|---|---|---|
| Dibucaine hydrochloride | 0.3 | g (7.90) |
| Diphenhydramine hydrochloride | 0.3 | g (10.3) |
| Sodium potassium tartrate | 0.5 | g |
| Chlorhexidine gluconate | 0.01 | g |
| Sodium hydroxide or hydrochloric acid | q.s. | (to pH 6.6) |
| Purified water | q.s. | |
| Total | 100 | mL |

[Example 8] Pharmaceutical Preparation for External Use

By a conventional method, the following components were mixed to form a solution to give a pharmaceutical preparation for external use.

| Dibucaine hydrochloride | 0.3 | g (7.90) |
| --- | --- | --- |
| Chlorpheniramine maleate | 0.5 | g |
| Oxalic acid | 0.5 | g |
| Chlorhexidine gluconate | 0.005 | g |
| Purified water | q.s. | |
| Total | 100 | mL |

[Example 9] Pharmaceutical Preparation for External Use

By a conventional method, the following components were mixed to form a solution to give a pharmaceutical preparation for external use.

| Dibucaine hydrochloride | 0.3 | g (7.90) |
| --- | --- | --- |
| Diphenhydramine hydrochloride | 0.5 | g (17.1) |
| Malic acid | 1.0 | g |
| Sodium hydroxide | q.s. | (to pH 5.0) |
| Purified water | q.s. | |
| Total | 100 | mL |

What is claimed is:

1. An aqueous pharmaceutical composition comprising an aqueous solution of stably maintained chlorhexidine gluconate, chloride ion and at least one pharmaceutically acceptable polycarboxylic acid of formula I:

$$HOOC—(CR_{i1}R_{i2})n—COOH \quad (I)$$

wherein n denotes an integer of 1 to 3; i denotes a positive integer not more than n; $R_{11}$, and $R_{12}$, when n=1, independently from each other, denote H, —OH or —COOH; each of $R_{11}$, $R_{12}$, $R_{21}$ and $R_{22}$, when n=2, denotes H, —OH or —COOH,
with the proviso that not all of them denote H simultaneously; and each of $R_{11}$, $R_{12}$, $R_{21}$, $R_{22}$, $R_{31}$ and $R_{32}$, when n=3, denotes H, —OH or —COOH, with the proviso that two adjacent carbons in no case contain four hydrogen atoms in total; or a pharmaceutically acceptable salt thereof.

2. The aqueous pharmaceutical composition of claim 1 which does not comprise a nonionic surface active agent.

3. The aqueous pharmaceutical composition of claim 1, wherein the concentration of said polycarboxylic acid is 0.01 to 5 W/V %.

4. The aqueous pharmaceutical composition of claim 3, wherein the concentration of chlorhexidine gluconate is 0.0001 to 0.05 W/V %.

5. The aqueous pharmaceutical composition of claim 4, wherein the concentration of chloride ion is 0.05 to 200 mEq/L.

6. The aqueous pharmaceutical composition of claim 1, wherein said polycarboxylic acid is selected from the group consisting of citric acid, oxalic acid, tartaric acid and malic acid.

7. A method for prevention of precipitation of chlorhexidine gluconate in an aqueous solution containing chloride ion and chlorhexidine gluconate, comprising adding to said aqueous solution at least one polycarboxylic acid of the formula I:

$$HOOC—(CR_{i1}R_{i2})n—COOH \quad (I)$$

wherein n denotes an integer of 1 to 3; i denotes a positive integer not more than n; $R_{11}$ and $R_{12}$, when n=1, independently from each other, denote H, —OH or —COOH; each of $R_{11}$, $R_{12}$, $R_{21}$ and $R_{22}$, when n=2, denotes H, —OH or —COOH, with the proviso that not all of them denote H simultaneously; and each of $R_{11}$, $R_{12}$, $R_{21}$, $R_{22}$, $R_{31}$ and $R_{32}$, when n=3, denotes H, —OH or —COOH, with the proviso that two adjacent carbons in no case contain four hydrogen atoms in total; or a pharmaceutically acceptable salt thereof.

8. The method of claim 7, wherein the concentration of said polycarboxylic acid is 0.01 to 5 W/V %.

9. The method of claim 7, wherein the concentration of chlorhexidine gluconate is 0.0001 to 0.05 W/V %.

10. The method of claim 7, wherein the concentration of chloride ion is 0.05 to 200 mEq/L.

11. The method of claim 7, wherein said polycarboxylic acid is selected from the group consisting of citric acid, oxalic acid, tartaric acid and malic acid.

12. The aqueous pharmaceutical composition of claim 2, wherein the concentration of said polycarboxylic acid is 0.01 to 5 W/V %.

13. The aqueous pharmaceutical composition of claim 2, wherein said polycarboxylic acid is selected from the group consisting of citric acid, oxalic acid, tartaric acid and malic acid.

14. The method of claim 8, wherein the concentration of chlorhexidine gluconate is 0.0001 to 0.05 W/V %.

15. The method of claim 8, wherein said polycarboxylic acid is selected from the group consisting of citric acid, oxalic acid, tartaric acid and malic acid.

16. The aqueous pharmaceutical composition of claim 1, wherein said polycarboxylic acid is in the form of a sodium, potassium, calcium or ammonium salt.

17. The aqueous pharmaceutical composition of claim 1, wherein the concentration of said polycarboxylic acid is 0.05–3 w/v %.

18. The aqueous pharmaceutical composition of claim 1, wherein the concentration of said chlorhexidine gluconate is 0.0001 to 0.025 w/v %.

19. The aqueous pharmaceutical composition of claim 2, wherein said polycarboxylic acid is in the form of a sodium, potassium, calcium or ammonium salt.

20. The aqueous pharmaceutical composition of claim 2, wherein the concentration of said chlorhexidine gluconate is 0.0001 to 0.025 w/v %.

21. The aqueous pharmaceutical composition of claim 2, wherein the concentration of said chlorhexidine gluconate is 0.0001 to 0.025 w/v %.

22. The method of claim 7, wherein said polycarboxylic acid is in the form of a sodium, potassium, calcium or ammonium salt.

23. The method of claim 7, wherein the concentration of said polycarboxylic acid is 0.05–3 w/v %.

24. The method of claim 7, wherein the concentration of said chlorhexidine gluconate is 0.0001 to 0.025 w/v %.

* * * * *